United States Patent [19]

Karjalainen et al.

[11] Patent Number: 4,568,686
[45] Date of Patent: Feb. 4, 1986

[54] SUBSTITUTED IMIDAZOLES AND THEIR USE

[75] Inventors: Arto J. Karjalainen; Kauko O. A. Kurkela, both of Oulu, Finland

[73] Assignee: Farmos Yhtyma Oy, Turku, Finland

[21] Appl. No.: 233,306

[22] Filed: Feb. 11, 1981

[30] Foreign Application Priority Data

Feb. 13, 1980 [GB] United Kingdom ................. 8004748

[51] Int. Cl.[4] .......................................... A61K 31/415
[52] U.S. Cl. .................................... 514/396; 514/399
[58] Field of Search .............. 548/343, 342, 335; 424/273; 514/396, 399

[56] References Cited

U.S. PATENT DOCUMENTS

| | | | |
|---|---|---|---|
| 3,188,315 | 6/1965 | Villani | 548/342 |
| 3,202,660 | 8/1965 | Zeile et al. | |
| 3,448,108 | 6/1969 | Villani | 548/342 |
| 4,006,243 | 2/1977 | Strehlke | 548/335 |
| 4,085,209 | 4/1978 | Miller et al. | 548/335 |
| 4,115,578 | 9/1978 | Miller et al. | 548/335 |
| 4,213,994 | 7/1980 | Gehert et al. | 548/343 |
| 4,260,626 | 4/1981 | Carr et al. | 548/335 |
| 4,275,071 | 6/1981 | Nardi et al. | 548/335 |
| 4,301,166 | 11/1981 | Regel et al. | 260/665 G X |

FOREIGN PATENT DOCUMENTS 1941761 2/1971 Fed. Rep. of Germany.

OTHER PUBLICATIONS

Baggaley et al., Journ. Med. Chem., vol. 18, No. 8, 1975, pp. 833-836.
Journ. Org. Chem., vol. 40, No. 2, pp. 252-255.
Dixit et al., Journ. Indian Chem. Soc., vol. 38, No. 10, 1961, pp. 853-857.
Hart et al., Aust. J. Chem. vol. 24, 1971, pp. 857-864.
Schubert et al., Wissenschaftliche Zeitschrift der Martin-Luther-Universität Halle-Wittenberg XI-5, May 1962, pp. 603-612.

Primary Examiner—Ethel G. Love
Attorney, Agent, or Firm—Armstrong, Nikaido, Marmelstein & Kubovcik

[57] ABSTRACT

The invention provides compounds of the formula:

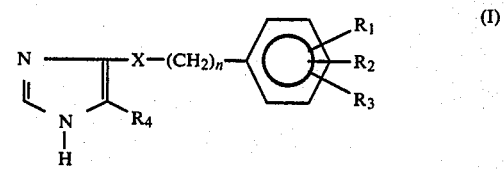

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbons atoms; X is

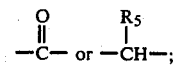

($R_5$ is hydrogen or hydroxy) and n is 1-4; and their non-toxic pharmaceutically acceptable acid additions salts. These compounds exhibit valuable pharmacological activity and are useful in the treatment of mammals, especially as anti-hypertensive agents. Furthermore, some of the compounds have proved to possess diuretic, β-blocking activity and/or antithrombotic activity. The compounds may be made by a variety of methods and may be incorporated in pharmaceutical compositions also comprising a compatible pharmaceutically acceptable carrier.

17 Claims, No Drawings

SUBSTITUTED IMIDAZOLES AND THEIR USE

DESCRIPTION

The present invention relates to substituted imidazole derivatives and their non-toxic, pharmaceutically acceptable acid addition salts, and their preparation, to pharmaceutical compositions containing the same, and to their use.

Known compounds possessing antihypertensive properties can be grouped, according to their pharmacological mechanism, as follows:

1. Diuretics, e.g., tienilic acid (U.S. Pat. No. 3,758,606), metolazone (U.S. Pat. No. 3,360,518) and bumetadine (U.S. Pat. No. 3,634,583);
2. Stimulants of central α-adrenergic receptors, e.g., clonidine (U.S. Pat. No. 3,202,660), imidazole derivatives [Jen et al, J.Med.Chem. 18 (1975), 90], guanabenz (German OLS No. 1,802,364), BS 100-141 (French Pat. No. 1,584,670), tiamenidine (German OLS No. 1,941,761), guanazodine (British Pat. No. 1,216,096) and guanethidine (U.S. Pat. No. 2,928,829);
3. α-Adrenergic blocking agents, e.g., prazosin (U.S. Pat. No. 3,511,836);
4. β-Adrenergic blocking agents, e.g., propranolol (U.S. Pat. No. 3,337,628) and metoprolol (German Pat. No. 2,106,209);
5. Dopamine-β-hydroxylase inhibitors, e.g., bupicomide (German OLS No. 2,217,084);
6. Norepinephrine-depleting drugs, e.g., MJ 10459-2 [Mathier et al, J.Med.Chem. 16 (1973) 901];
7. Inhibitors of the renin-angiotensin system, e.g., saralasine (German Pat. No. 2,127,393); and captopril (Svensk Farm.Tidskr. 83 (1979) 71); and
8. Peripheral vasodilators, e.g., minoxidil (U.S. Pat. No. 3,644,364).

Of 4-substituted arylalkylimidazole derivatives related to the compounds of this invention only 4-[2-(phenyl)-ethyl]-imidazole (C.A. 56:14256a, C.A. 60:14495e) and 4-[2-(3′,4′-dimethoxyphenyl)ethyl]-5-methyl-imidazole (C.A. 74:142135z) have been previously described. However, the prior art does not disclose any pharmaceutical utility for these compounds.

The imidazole derivatives of the present invention have the general formula:

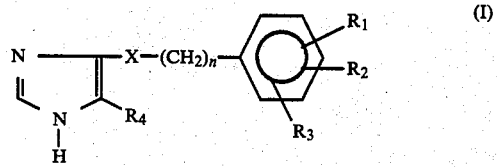

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; X is

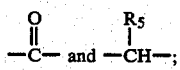

$R_5$ is hydrogen or hydroxy; and n is an integer from 1 to 4. The non-toxic pharmaceutically acceptable acid addition salts of these compounds are also within the scope of the invention.

The compounds of the formula (I) form acid addition salts with both organic and inorganic acids. They can thus form many pharmaceutically usable acid addition salts, such as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one of the compounds of formula (I) or a non-toxic, pharmaceutically acceptable acid addition salt thereof, and a compatible pharmaceutically acceptable carrier therefor.

The present invention provides, for example, the following specific compounds of formula (I) wherein X represents —$CHR_5$— and $R_5$ is hydrogen:

4-[2-(2′-methylphenyl)-ethyl]-imidazole
4-[2-(3′-methylphenyl)-ethyl]-imidazole
4-[2-(4′-methylphenyl)-ethyl]-imidazole
4-[2-(2′,3′-dimethylphenyl)-ethyl]-imidazole
4-[2-(2′,6′-dimethylphenyl)-ethyl]-imidazole
4-[2-(2′,4′-dimethylphenyl)-ethyl]-imidazole
4-[2-(2′,5′-dimethylphenyl)-ethyl]-5-methyl-imidazole
4-[2-(2′,5′-dimethylphenyl)-ethyl]-imidazole
4-[2-(3′,4′-dimethylphenyl)-ethyl]-imidazole
4-[2-(3′,4′-dimethylphenyl)-ethyl]-5-methyl-imidazole
4-[2-(2′,4′6′-trimethylphenyl)-ethyl]-imidazole
4-[2-(2′-ethylphenyl)-ethyl]-imidazole
4-[2-(2′,6′-diethylphenyl)-ethyl]-imidazole
4-[2-(2′-methoxyphenyl)-ethyl]-imidazole
4-[2-(2′-chlorophenyl)-ethyl]-imidazole
4-[2-(3′-chlorophenyl)-ethyl]-imidazole
4-[2-(4′-chlorophenyl)-ethyl]-imidazole
4-[2-(2′,6′-dichlorophenyl)-ethyl]-imidazole
4-[2-(2′,3′-dichlorophenyl)-ethyl]-imidazole
4-[2-(2′,6′-dibromophenyl)-ethyl]-imidazole
4-[2-(2′,6′-difluorophenyl)-ethyl]-imidazole
4-[2-(2′-methylphenyl)-ethyl]-5-methyl-imidazole
4-[2-(2′,6′-dimethylphenyl)-ethyl]-5-methyl-imidazole
4-[3-(phenyl)-propyl]-imidazole
4-[3-(2′-methylphenyl)-propyl]-imidazole
4-[3-(3′-methylphenyl)-propyl]-imidazole
4-[3-(4′-methylphenyl)-propyl]-imidazole
4-[3-(2′,3′-dimethylphenyl)-propyl]-imidazole
4-[3-(2′,6′-dimethylphenyl)-propyl]-imidazole
4-[3-(2′-chlorophenyl)-propyl]-imidazole
4-[3-(2′,6′-dichlorophenyl)-propyl]-imidazole
4-[4-(2′-methylphenyl)-butyl]-imidazole
4-[4-(3′-methylphenyl)-butyl]-imidazole
4-[4-(2′,3′-dimethylphenyl)-butyl]-imidazole
4-[4-(2′,6′-dimethylphenyl)-butyl]-imidazole
4-[4-(2′,6′-dichlorophenyl)-butyl]-imidazole
4-[5-(2′-methylphenyl)-pentyl]-imidazole
4-[5-(2′,6′-dimethylphenyl)-pentyl]-imidazole
4-[5-(2′,6′-dichlorophenyl)-pentyl]-imidazole The following specific compounds of formula (I) wherein X represents —$CHR_5$— and $R_5$ is hydroxy:

4-[2-(2′-methylphenyl)-1-hydroxyethyl]-imidazole
4-[2-(3′-methylphenyl)-1-hydroxyethyl]-imidazole
4-[2-(4′-methylphenyl)-1-hydroxyethyl]-imidazole
4-[2-(2′,6′-dimethylphenyl)-1-hydroxyethyl]-imidazole
4-[2-(2′,3′-dimethylphenyl)-1-hydroxyethyl]-imidazole
4-[2-(2′-ethylphenyl)-1-hydroxyethyl]-imidazole
4-[2-(2′,6′-diethylphenyl)-1-hydroxyethyl]-imidazole
4-[2-(2′-chlorophenyl)-1-hydroxyethyl]-imidazole
4-[2-(2′,6′-dichlorophenyl)-1-hydroxyethyl]-imidazole
4-[2-(2′,6′-dibromophenyl)-1-hydroxyethyl]-imidazole
4-[2-(2′-methylphenyl)-1-hydroxyethyl]-5-methyl-imidazole 4-[2-(2',6'-dimethylphenyl)-1-hydroxyethyl]-5-methyl-imidazole
4-(3-phenyl-1-hydroxypropyl)-imidazole
4-[3-(2'-methylphenyl)-1-hydroxypropyl]-imidazole
4-[3-(3'-methylphenyl)-1-hydroxypropyl]-imidazole
4-[3-(4'-methylphenyl)-1-hydroxypropyl]-imidazole
4-[3-(2',3'-dimethylphenyl)-1-hydroxypropyl]-imidazole
4-[3-(2',4'-dimethylphenyl)-1-hydroxypropyl]-imidazole
4-[3-(2',6'-dimethylphenyl)-1-hydroxypropyl]-imidazole
4-[3-(2',6'-dimethylphenyl)-1-hydroxypropyl]-5-methyl-imidazole
4-[4-(2'-methylphenyl)-1-hydroxybutyl]-imidazole
4-[4-(2',4'-dimethylphenyl)-1-hydroxybutyl]-imidazole
4-[4-(2',6'-dimethylphenyl)-1-hydroxybutyl]-imidazole
4-[5-(2'-methylphenyl)-1-hydroxypentyl]-imidazole
4-[5-(2',6'-dimethylphenyl)-1-hydroxypentyl]-imidazole
4-[3-(2',4',6'-trimethylphenyl)-1-hydroxypropyl]-imidazole
4-[3-(4'-ethylphenyl)-1-hydroxypropyl]-imidazole
4-(2-phenyl-1-hydroxyethyl)-imidazole
4-[4-(2',6'-dichlorophenyl)-1-hydroxybutyl]-imidazole
4-[2-(2',6'-dichlorophenyl)-1-hydroxyethyl]-5-methyl-imidazole
4-[2-(2'-chlorophenyl)-1-hydroxyethyl]-5-methyl-imidazole
4-[3-(2',3'-dimethylphenyl)-1-hydroxypropyl]-5-methyl-imidazole
4-(3-phenyl-1-hydroxypropyl)-5-methyl-imidazole
4-(2-phenyl-1-hydroxyethyl)-5-methyl-imidazole
4-[2-(2',3'-dimethylphenyl)-1-hydroxyethyl]-5-methyl-imidazole
4-[3-[4'-methylphenyl)-1-hydroxypropyl]-5-methyl-imidazole
4-[3-(3'-methylphenyl)-1-hydroxypropyl]-5-methyl-imidazole
4-[3-(4'-methoxyphenyl)-1-hydroxypropyl]-5-methyl-imidazole
4-[2-(2',5'-dimethylphenyl)-1-hydroxyethyl]-5-methyl-imidazole
4-[2-(3',4'-dimethylphenyl)-1-hydroxyethyl]-5-methyl-imidazole
and the following specific compounds of formula (I) wherein X represents

4-[2-(2',6'-dimethylphenyl)-1-oxoethyl]-imidazole
4-[2-(2',6'-dichlorophenyl)-1-oxoethyl]-imidazole
4-[2-(2',6'-dichlorophenyl)-1-oxoethyl]-5-methyl-imidazol
4-[3-(2'-methylphenyl)-1-oxopropyl]-imidazole
4-[2-(2'-chlorophenyl)-1-oxoethyl]-imidazole
4-[3-(2'-chlorophenyl)-1-oxopropyl]-imidazole
4-[3-(3'-methylphenyl)-1-oxopropyl]-imidazole
4-[3-(4'-methylphenyl)-1-oxopropyl]-imidazole
4-[3-(2',6'-dimethylphenyl)-1-oxopropyl]-imidazole
4-[3-(2',3'-dimethylphenyl)-1-oxopropyl]-imidazole
4-[5-(2',6'-dimethylphenyl)-1-oxopentyl]-imidazole The compounds of the present invention have been found to possess excellent antihypertensive properties. Preliminary tests have shown that they also possess other valuable pharmacological properties, for example, β-blocking, antithrombotic and diuretic activity.

While all of the compounds of formula (I) have the aforementioned activities, certain groups of compounds remain preferred. One such preferred group can be represented by the structural formula:

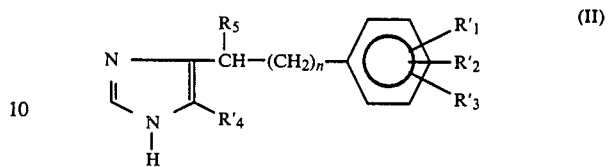

wherein $R_5$ and n are the same as before; each of $R'_1$, $R'_2$ and $R'_3$, is hydrogen, chloro, methyl, ethyl, methoxy or hydroxy; and $R'_4$ is hydrogen or methyl. Particularly preferred antihypertensives are those compounds of formula (II) above wherein $R'_1$, $R'_2$, $R'_3$ and $R'_5$ are the same as before and $R'_4$ is hydrogen.

β-blocking activity has been found particularly in compounds of formula (II) above, wherein $R_5$ is hydroxy, $R'_1$, $R'_2$ and $R'_3$ are as before and $R'_4$ is alkyl, preferably methyl.

Diuretic activity has been found particularly in compounds of formula (II), wherein $R_5$ is hydroxy, $R_1'$, $R_2'$ and $R_3'$ are as before and $R_4'$ is hydrogen.

According to a feature of the invention, the compounds of formula (I) in which X is —CHOH— or —CO— are made by a Grignard reaction in which an imidazole aldehyde of the formula:

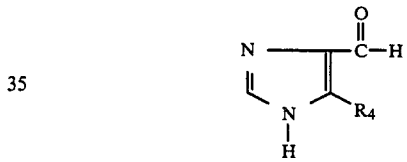

wherein $R_4$ is as defined before, is reacted with an arylalkyl magnesium halide derivative of the formula:

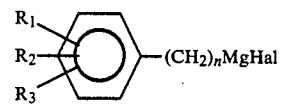

wherein $R_1$, $R_2$, $R_3$, $R_4$ and n are as defined before and Hal is a halogen atom. This reaction gives not only the expected product in which X is —CHOH— but also the corresponding product in which X is —CO—.

The arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofuran. The arylalkylmagnesiumhalide derivative is prepared in the usual way by adding the arylalkylmagnesiumhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4-imidazole derivative is added in solid form in small portions. After the addition, the reaction mixture is refluxed until all of the 4-imidazole derivative has reacted. The reaction time varies between one and five hours. In the reaction, at least two equivalents of arylalkylmagnesiumhalide are used per one equivalent of 4-imidazolealdehyde, because the last mentioned compound contains active hydrogen which binds a part of the Grignard reagent.

The above described Grignard reaction utilizing a 4-imidazolealdehyde as starting material is a surprising and new method for the synthesis of imidazole derivatives. The process is surprising in view of the teachings of the prior art. Thus, for example, Deulofeu et al., *J.Org.Chem.*, 1949, 915 states that 4-imidazolealdehyde does not react with methylmagnesiumiodide, i.e., in the Grignard reaction.

It is further surprising that in the above described Grignard reaction a compound of the formula (III)

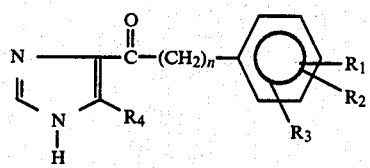
(III)

wherein $R_1$, $R_2$, $R_3$, $R_4$ and n are the same as before, is formed. The amount of the compound of the formula (III), which can be isolated from the reaction mixture depends on the structure of the derivative, the reaction time, and the amount of Grignard reagent used. Thus when one and a half equivalents of a longer chained Grignard reagent are reacted with the aldehyde derivative using relatively shorter reaction times than usually, from about one half to two hours, the amount of the compound of formula (III) can be as high as 50% of the isolated products.

Another process for the preparation of compounds of the present invention, in which X is —CHOH— comprises reducing a compound of the formula (III) to a compound of formula (I) wherein X is —CHOH—. The reduction is performed by usual methods, for example using sodium borohydride in ethanol.

A two-stage process for the preparation of compounds of the present invention wherein X is —CH$_2$— comprises a first stage wherein a compound of the formula (I) in which X is —CHOH— is dehydrated to a compound of the formula (IV)

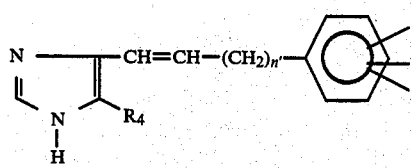
(IV)

wherein $R_1$, $R_2$, $R_3$ and $R_4$ are defined as before and n' is 0–3, and a second stage, wherein the compound of the formula (IV) is hydrogenated to a compound of the formula (I) in which X is —CH$_2$—.

The dehydration is preferably performed by refluxing in an appropriate acidic solution, e.g. concentrated hydrochloric acid. In the second stage the hydrogenation is conveniently carried out at room temperature with good stirring in the above mentioned acidic solution in the presence of a catalyst in a hydrogen atmosphere. Suitable catalysts are for example platinum oxide, palladium-on-carbon or Raney-nickel.

Yet another process for the preparation of the compounds of formula (I) in which X is —CH$_2$— comprises reacting formamide with a benzene derivative of the formula:

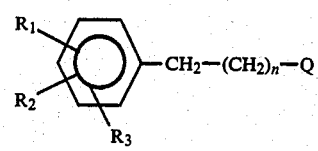

wherein $R_1$, $R_2$, $R_3$ and n are as defined hereinabove, and Q is a radical of formula:

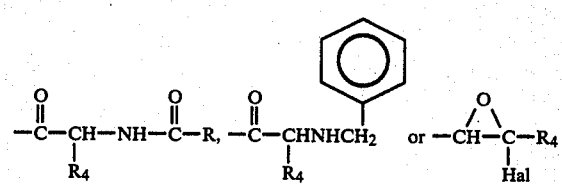

wherein R is a substituted and unsubstituted alkyl, arylalkyl or aryl group, and $R_4$ and Hal are as defined hereinabove. Preferably the reaction is performed by vigorously boiling the benzene derivative in formamide, the reaction time varying with the particular material employed.

Reaction times typically are from 30 minutes to 8 hours. Obviously, the formamide treatment will be followed by reaction with an appropriate acid (e.g. HCl) when Q in the starting material is $$-\overset{O}{\underset{}{C}}-\underset{R_4}{CH}-NH-\overset{O}{\underset{}{C}}-R$$

in order to obtain the corresponding compound of formula (I).

Similarly, when a starting material wherein Q is $$-\overset{O}{\underset{}{C}}-\underset{R_4}{CHNHCH_2}-\bigcirc$$

is employed, then the formamide treatment will be followed by hydrogenation, thus affording the desired compound of formula (I).

A further process for the preparation of the compounds of the formula (I) in which X is —CH$_2$— comprises hydrolysing a corresponding compound of the formula:

wherein $R_1$, $R_2$, $R_3$, $R_4$ and n are as defined before and $R_6$ is an alkyl group of 1 to 7 carbon atoms or an aryl radical of 6 to 10 carbon atoms. Preferably, the hydrolysis is carried out by boiling the starting material, an N-acylated imidazole derivative, in an aqueous solution of an inorganic acid until the reaction is completed.

Yet another process for the preparation of the compounds of formula (I) in which X is —CH₂—, comprises hydrogenating a starting material of the formula:

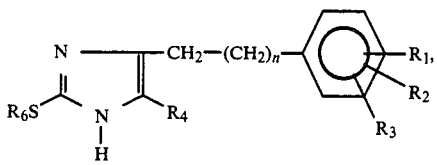

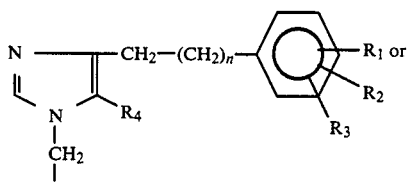

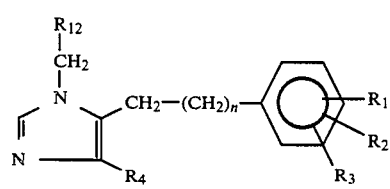

wherein $R_1$, $R_2$, $R_3$, $R_4$, n and $R_6$ are as defined before and $R_{12}$ is an aryl group. The hydrogenation is conveniently conducted in the presence of a suitable catalyst and under a hydrogen atmosphere, with stirring or using metallic sodium in liquid ammonia. Suitable catalysts include platinum oxide, palladium-on-carbon and Raney nickel. Reaction temperatures vary with the particular starting material employed, with typical temperatures being 25°–70° C.

The present invention further provides yet another process for preparing compounds of the invention in which $R_4$ is hydrogen and X is —CH₂—. Thus, according to this embodiment of the invention, a starting material of the formula V:

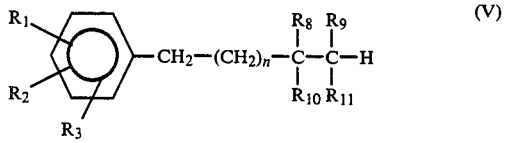 (V)

wherein $R_1$, $R_2$, $R_3$ and n are as hereinbefore defined; wherein $R_8$, $R_9$, $R_{10}$ and $R_{11}$, which can be the same or different, are each hydrogen, hydroxy, halogen, amino, —O— alkyl of 1 to 7 carbon atoms or

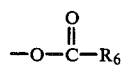

wherein $R_6$ is defined as before; or wherein $R_8$ and $R_{10}$ can be combined to form an oxo group, or $R_9$ and $R_{11}$ can be combined to form an oxo group, or both $R_8$ and $R_{10}$ and $R_9$ and $R_{11}$ can simultaneously form oxo groups; is reacted with a reagent capable of converting said starting material to the corresponding imidazole of the formula:

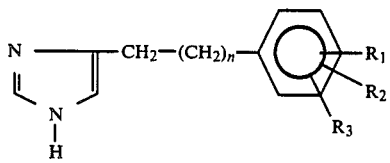

wherein $R_1$, $R_2$, $R_3$ and n are defined as before. Reagents capable of converting the depicted starting material to the corresponding imidazole include NH₃+CH₂O (or a source of ammonia and formaldehyde); NH=CH—NH₂;

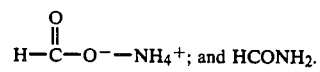

Choice of an appropriate reagent varies with the particular starting material employed. For instance, when the starting material is a haloketone or haloaldehyde, for example, when $R_8$ and $R_{10}$ together form a keto group, $R_9$ is bromine and $R_{11}$ is hydrogen, or when $R_9$ and $R_{11}$ form a keto group, $R_8$ is bromine and $R_{10}$ is hydrogen, then it is preferable to react the starting material with formamide in order to obtain the 4-arylalkylimidazole derivative.

It is likewise preferable to employ formamide as the reagent in cases where, in place of the bromine atom in the aforementioned starting materials, there is instead a hydroxyl, amino or acetyl group. In these instances, formamide is used in excess and acts in part as the solvent. Generally, the reaction is run at the boiling point of formamide for a period of time ranging from one to five hours.

If the starting material is a glyoxal derivative, e.g., benzyl glyoxal or other compound of the type:

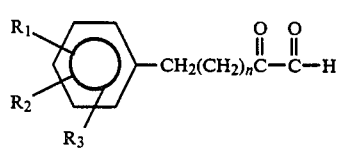

then the ammonia needed for the synthesis of the imidazole ring is suitably taken from ammonium acetate, while the needed formalin is taken from hexamethylenetetramine; two equivalents of these reagents are used per equivalent of glyoxal derivative. Suitable solvents are, for example, dimethylformamide and formamide. Typically, the reaction temperature is the boiling point of the reaction mixture, and the reaction time is usually from one to three hours. Alternatively, the glyoxal derivative can be reacted directly with ammonia and formaldehyde, or with formamide, but the yields of desired product are generally lower.

A surprising aspect of the above mentioned reaction is the fact that the hydroxyacetal starting materials, e.g., compounds of the formula:

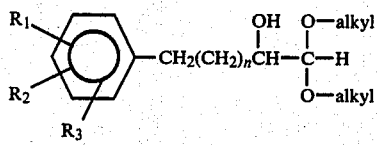

very readily react with formamide to form the corresponding imidazoles (ref. example 35c).

As a variation of the above described process, a starting material of formula (V) can be treated with an appropriate reagent, particularly formamide, under milder conditions than those discussed above, allowing isolation of the intermediate oxazole, which can then be further reacted with formamide to afford the corresponding compound of formula (I).

In this variation, the first formamide treatment is carried out at a low temperature (80°–120° C., depending on the particular starting material employed), to afford an oxazole of the formula:

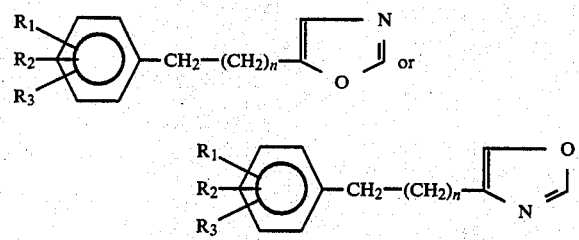

which can then be easily reacted with formamide, typically at about 180° C., for about 4 hours, to afford the desired compound of the present invention.

Yet another method for the preparation of the compounds of formula (I) wherein X is —CH$_2$— comprises reacting a N-trialkylsilylimidazole of the formula

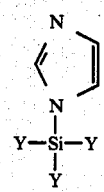

wherein Y is an alkyl group, preferably methyl, with an arylalkylhalogenide of the formula

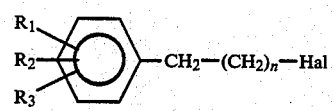

wherein $R_1$, $R_2$, $R_3$ and n are as before and Hal is a halogen atom, in the presence of a Lewis acid, for example titanium tetrachloride, aluminium chloride or zinc chloride. As solvent can be used for example methylene chloride or chloroform. The reaction is preferably carried out at room temperature stirring the starting materials for 6–12 hours.

The starting materials of formula (V) can be prepared by known methods. Reference is made to Examples 35(a) and (b) set forth hereinafter for a description of methods which have been employed to prepare various starting materials of formula (V), it being understood that such examples are simply illustrative of procedures which can be utilized to prepare the desired starting materials.

As stated herein above, the compounds of the general formula (I) and their non-toxic, pharmaceutically acceptable acid addition salts have valuable pharmacological properties and have been found to possess excellent anti-hypertensive activity in mammals. This activity makes these imidazole derivatives particularly useful in the treatment of high blood pressure.

Preliminary tests have shown that they also possess other pharmacological properties as well, for example, β-blocking, antithrombotic and diuretic activity.

Administration of isomeric compounds of formula (I), their non-toxic, pharmaceutically acceptable acid salts or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc,. and of course the structure of the derivative.

One of the most potent anti-hypertensive derivatives of the invention is 4-[2-(2',6'-dimethylphenyl)-ethyl-]imidazole, the daily dose, orally administered of which generally ranges from about 0.3–0.7 milligrams per kilogram of mammal.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The anti-hypertensive properties of the imidazole derivatives of the present invention have been determined by the following procedure. Sprague-Dawley rats of normal weight were first anesthetized with urethane. After this, the femoral artery was connected by way of a polyethylene tube with a blood pressure transducer. The test substance was then injected into the femoral vein and the blood pressure and the pulse frequency were registered with a recorder.

In a further test for anti-hypertensive properties unanesthetized Vistar spontaneous hypertensive rats (SHR) were used. The test derivative was administered perorally by way of a tube into the stomach. The blood pressure was measured from the tail using an indirect bloodless method.

In another experiment 3 months old spontaneous hypertensive male rats were used to test the anti-hypertensive properties during a period of 4 weeks. The test derivative was administered daily to each rat in the drinking water and the blood pressure of the tail was measured by a standard electric method.

In additional tests the anti-hypertensive effect was studied on dogs. In these tests single doses were administered intravenously and the blood pressure was measured intra-arterially and intravenously.

The β-blocking activity was measured in vitro as follows: The atrium of a guinea-pig was isolated. The inhibiting activity of the compound against isoprenaline-induced chronotropic and inotropic action in the isolated atrium was measured. The antithrombotic activity was investigated in vitro. The inhibiting activity of the compounds against ADP- and collagen-induced aggregation of thrombocytes was measured. In the test thrombocytes from a cow was used. To 1.2 ml of plasma containing 250000 thrombocytes/mm$^3$ were added 50 μl of a solution of the compound to be tested. After 10 min incubation either ADP or collagen was added. The aggregation of the thrombocytes was turbidimetrically determined at λ=605 n m.

Acute toxicity was determined by using female mice of NMRI-Strain with an age of about 7 months and weighing 30–40 g. The administration of the test compound was i.v.

Thus, 4-[2-(2',6'-dimethylphenyl)-ethyl]-imidazole, which has a LD$_{50}$ value of 60 mg/kg i.v., was found in the blood pressure study with anesthetized rats of normal weight described above to cause a registrable lowering of the blood pressure with a dose of 30 μg/kg i.v. With a dose of 100 μg/kg i.v. the blood pressure lowering was quite clear and with a dose of 300 μg/kg i.v. the reduction of blood pressure was on an average 20 percent, the decrease of pulse frequency being 15 percent on an average. The duration of the effect was at least 60 minutes (after which time the determination was interrupted). As the LD$_{50}$ is 60 mg/kg i.v. in mice, it can be concluded that the therapeutic range is very broad. When the anti-hypertensive effect of the compound was determined with awake SHR-rats, it was found that the decrease of blood pressure was about 15 percent with a dose of 3 mg/kg p.o. and 20 percent with a dose of 5 mg/kg p.o. one hour after the administration. In the test for anti-hypertensive properties during a 4 weeks period with spontaneous hypertensive rats was found that with a dose of 250 μg/kg daily p.o. a significant reduction of blood pressure was achieved. In toxicological experiments performed at the same time was found that a dose of 10 mg/kg daily of the compound did not give any toxic symptoms. Also from these experiments can thus be deduced that the therapeutic range of the compound is very broad.

Furthermore the reduction of the blood pressure in the performed test was observed to be smooth and of long duration. In the tests with dogs was found that a dose of 30 μg/kg i.v. gave a 20 percent long-lasting decrease of the blood pressure.

The compound 4-[2-(2'-methylphenyl)-ethyl]-imidazole, which has a LD$_{50}$ value of 50 mg/kg i.v. in mice, caused a blood pressure lowering of 25 percent measured one hour after the administration with a dose of 10 mg/kg p.o. The duration of the effect was long-lasting, at least 6 hours (after which time the determination was interrupted).

For the compound 4-[2-(2',6'-dichlorophenyl)-ethyl]-imidazole having a LD$_{50}$ of 50 mg/kg i.v. in mice the lowering of the blood pressure was 30 percent measured 30 minutes after administration with a dose of 0.4 mg/kg i.v.

For the compound 4-[3-(2',6'-dimethylphenyl)-propyl]-imidazole having a LD$_{50}$ of 25 mg/kg i.v. in mice, the following results in the above mentioned tests were obtained: lowering of blood pressure with a dose of 100 μg/kg i.v. of 13 percent, 30 minutes after administration; lowering of blood pressure with a dose of 10 mg/kg p.o. of 18 percent one hour after administration. The duration of the effect was long-lasting, in the latter case for example at least 6 hours.

The compound 4-[4-(2',6'-dimethylphenyl)-butyl]-imidazole, having a LD$_{50}$ of 135 mg/kg i.v. in mice, produced a decrease in the blood pressure of about 10 percent, with a dose of 10 mg/kg p.o. (one hour after administration).

For the compound 4-[2-(2'-chlorophenyl)-hydroxyethyl]-imidazole having a LD$_{50}$ of 110 mg/kg i.v. in mice, the lowering of blood pressure was 30 percent, measured 30 minutes after administration with a dose of 0,7 mg/kg i.v.

For the compound 4-[2-(2',6'-dimethylphenyl)-hydroxyethyl]-imidazole having a LD$_{50}$ of 130 mg/kg i.v. in mice, the lowering of blood pressure was 25 percent, measured 30 minutes after administration with a dose of 0.1 mg/kg i.v.

For the compound 4-[2-(2',6'-dimethylphenyl)-1-oxoethyl]-imidazole having a LD$_{50}$ of 150 mg/kg i.v. in mice, the lowering of blood pressure was 15 percent, measured one hour after administration with a dose of 20 mg/kg p.o.

The compound 4-[2-(2',3'-dimethylphenyl)-ethyl]-imidazole, which has a LD$_{50}$ value of 45 mg/kg i.v. in mice, caused a blood pressure lowering of 20 percent measured 30 minutes after the administration with a dose of 1 mg/kg i.v. A pulse frequence lowering of 20% was obtained 30 minutes after the administration of 3 mg/kg i.v.

The compound 4-[2-(2',6'-diethylphenyl)-ethyl]-imidazole which had a LD$_{50}$ value of 60 mg/kg, i.v. in mice caused a blood pressure lowering already with a dose of 0.03–0.1 mg/kg i.v. A blood pressure drop of 20% was measured 30 minutes after the administration with a dose of 1–3 mg/kg i.v.

In the β-blocking activity test, the compound 4-[2-(2',6'-dichlorophenyl)-1-hydroxyethyl]-5-methylimidazole caused at a concentration of 1 μg/ml a 68 percent inhibition of isoprenaline induced chronotropic effect and 59 percent inhibition of isoprenaline induced inotropic effect. The compound was β$_1$-selective. LD$_{50}$ was 75 mg/kg in mice.

In the antithrombotic activity test, each of the compounds 4-[2-(2',6'-dimethylphenyl)-ethyl]-5-methylimidazole, 4-[2-(2',6'-dichlorophenyl)-1-hydroxyethyl]-5-methylimidazole and 4-[2-(2',6'-diethylphenyl)-ethyl]-imidazole inhibited the collagen-induced aggregation of thrombocytes completely and the ADP-induced aggregation clearly.

The compound 4-[2-(2',6'-dimethylphenyl)-1-hydroxyethyl]-imidazole gave in rats a diuretic effect of 161 percent (5 h after administration) at dose of 4 mg/kg i.p. injection. Before the test the rats were fasting over night and got 10 ml water p.o. immediately before the injection. This compound has proved to be effective in diuretic tests with dogs, too.

In the Examples below, where $^1$H-NMR spectrum shifts are presented, the NMR spectra were determined with a Perkin-Elmer R 24 apparatus using an external tetramethylsilane standard, from which the presented chemical shifts (δ, ppm) are tabulated. The latters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide. The presented $^{13}$C-NMR-spectrum were determined with a Jeol FX-100 apparatus.

The mass-spectra were determined with a Perkin-Elmer RMU apparatus using direct inlet system. The temperature employed was the lowest temperature needed for the evaporation of the compound as base. In the examples the strongest and the most essential fragment-ions from a structural viewpoint are given as m/e values. In parenthesis is given the intensity of the fragment-ion in relation to the main peak.

The following Examples illustrate the invention.

EXAMPLE 1

4-[3-(2',6'-dimethylphenyl)-1-hydroxypropyl]-imidazole 4.8 g of dry magnesium turnings are covered with 100 ml of dry tetrahydrofuran (THF). The mixture is heated to boiling and a solution of 42.6 g of 2-(2',6'-dimethylphenyl)-1-bromoethane in 100 ml of dry tetrahydrofuran is added dropwise at such a rate that gentle refluxing is maintained. After the addition is complete, the reaction mixture is refluxed for an additional 30 minutes.

The reaction mixture is cooled to 50° C. and 7.0 g of 4-imidazolealdehyde is added slowly in small portions. After the addition is complete, the mixture is refluxed for 5 hours. Then the reaction mixture is cooled and poured into 200 ml of cold water containing 20 ml of concentrated hydrochloric acid. Part of the tetrahydrofuran is distilled off to give a smaller volume and the tetrahydrofuran is replaced with water. The mixture is washed twice with 50 ml portions of chloroform. The aqueous layer is made alkaline with sodium hydroxide solution (pH about 8). The precipitate which forms is washed with water and added to 100 ml of 4N NaOH solution and the mixture is stirred vigorously for one hour. The precipitate is filtered, washed several times with water and dried. The crude product is recrystallized from a mixture of water and ethanol to give 10.1 g of a product melting at 157°–158° C.

$^1$H-NMR: 2.3 (m, 2H), 2.6 (s, 6H), 3.0 (m, 2H), 5.15 (t, 1H), 5.45 (s, 2H) 7.25 (s, 3H), 7.35 (s, 1H), 8.0 (s, 1H)

MS: 230 (21%), 212 (20%), 197 (13%), 133 (11%), 124 (7%), 119 (18%), 118 (23%), 117 (18%), 115 (11%), 111 (98%), 98 (100%), 97 (69%), 95 (8%), 93 (7%), 91 (21%), 82 (27%), 81 (10%)

EXAMPLE 2

4-[3-(2',6'-dimethylphenyl)-1-oxopropyl]-imidazole

The method described in Example 1 is followed except that 9.6 g of 4-imidazolealdehyde is used. The precipitate at pH about 8 is added to 4N sodium hydroxide solution and the mixture is stirred vigorously for one hour and filtered. The filtrate is neutralized with hydrochloric acid and the precipitate is filtered. The filter cake is washed with water and dried. The yield of crude product is 9.5 g and melts at 132°–148° C. The product is converted to its hydrochloride in ethyl acetate. The melting point is 172°–178° C.

$^1$H-NMR (HCl-salt): 2.35 (s, 6H), 3.1 (s, 4H), 4.55 (s, 2H), 7.0 (s, 3H), 8.15 (s, 1H), 8.55 (s, 1H)

EXAMPLE 3

4-[3-(2',6'-dimethylphenyl)-1-hydroxypropyl]-imidazole 2.3 g of 4-[3-(2',6'-dimethylphenyl)-1-oxopropyl]-imidazole is dissolved in 20 ml of ethanol. 1.0 g of sodium borohydride is added with stirring at room temperature. After the addition the mixture is stirred for 4 hours at room temperature, then evaporated to dryness. 30 ml of water is added to the residue and the resultant mixture is stirred and cooled. The precipitate is filtered and washed with water. The yield is 2.1 g of 4-[3-(2',6'-dimethylphenyl)-1-hydroxypropyl]-imidazole.

In the Examples 4–27 the procedure of Example 1 is repeated except that in place of 2-(2',6'-dimethylphenyl)-1-bromoethane is used the corresponding (substituted phenyl)-1-bromoalkane and in the Examples 13, 14, 16, 18, 19, 20 and 27 is used 5-methyl-4-imidazolealdehyde in place of 4-imidazolealdehyde.

EXAMPLE 4

4-[3-(2',4'-dimethylphenyl)-1-hydroxypropyl]-imidazole

M.p. 70°–74° C. (from water-ethanol)
$^1$H-NMR: 2.0 (m, 2H), 2.2 (s, 6H), 2.6 (m, 2H), 4.5 (t, 1H), 5.2 (s, 2H), 6.9 (m, 4H), 7.6 (s, 1H)

EXAMPLE 5

4-(1-hydroxy-3-phenylpropyl)-imidazole

M.p. 144°–146° C. (from water). M.p. at the hydrochloride 153°–155° C. (from isopropanol).
$^1$H-NMR: 2.25 (m, 2H), 2.7 (m, 2H), 4.75 (t, 1H), 5.15 (s, 2H) 7.0 (s, 1H), 7.25 (s, 5H), 7.65 (s, 1H)
MS: 202 (8%), 181 (13%), 183 (6%), 169 (3%), 156 (3%), 115 (4%) 111 (10%), 98 (100%), 97 (76%), 91 (16%), 82 (7%)

EXAMPLE 6

4-[3-(2',3'-dimethylphenyl)-1-hydroxypropyl]-imidazole

M.p. 130°–134° C.
$^1$H-NMR (HCl): 2.1 (m, 2H), 2.15 (s, 3H), 2.25 (s, 3H), 2.7 (m, 2H), 4.85 (t, 1H), 5.1 (s, 2H), 6.95 (s, 3H), 7.4 (s, 1H), 8.7 (s, 1H).

EXAMPLE 7

4-[3-(3'-methylphenyl)-1-hydroxypropyl]-imidazole
M.p. 104°–106° C.
$^1$H-NMR: 2.15 (m, 2H), 2.3 (s, 3H), 2.6 (m, 2H), 4.7 (t, 1H), 5.1 (s, 2H), 7.0 (m, 5H), 7.6 (s, 1H).

EXAMPLE 8

4-[3-(4'-methylphenyl)-1-hydroxypropyl]-imidazole
M.p. 120°–124° C.
$^1$H-NMR: 2.2 (m, 2H), 2.3 (s, 3H), 2.65 (m, 2H), 4,75 (t, 1H), 5.15 (s, 2H), 7.05 (m, 5H), 7.65 (s, 1H).

EXAMPLE 9

4-[3-(2'-methylphenyl)-1-hydroxypropyl]-imidazole
M.p. of the hydrochloride 164°–166° C. (from isopropanol-ethylacetate)
$^1$H-NMR (HCl-salt): 1.9 (m, 2H), 2.1 (s, 3H), 2.55 (m, 2H), 4.6 (s, 3H), 4.8 (t, 1H), 7.0 (s, 4H), 7.2 (s, 1H), 8.5 (s, 1H).

EXAMPLE 10

4-[5-(2',6'-dimethylphenyl)-1-hydroxypentyl]-imidazole

M.p. 129°–134° C.

$^1$H-NMR (trifluoroacetic acid is added): 1.2–1.9 (m, 6H), 2.5 (s, 6H), 4.3 (t, 1H), 5.5 (s, 2H), 6.8 (s, 3H), 7.35 (s, 1H), 8.65 (s, 1H)

EXAMPLE 11

4-[2-(2'-chlorophenyl)-1-hydroxyethyl]-imidazole

M.p. of hydrochloride 164°–167° C.

$^1$H-NMR (trifluoroacetic acid is added): 3.85 (d, 2H), 5.1 (t, 1H), 5.5 (2H), 7.0 (s, 1H), 7.25 (m, 4H), 7.65 (s, 1H)

EXAMPLE 12

4-[2-(2',6'-dichlorophenyl)-1-hydroxyethyl]-imidazole

Melting point 138°–141° C. Melting point of hydrochloride 201°–203° C. (from water)

$^1$H-NMR (HCl-salt): 3.4 (d, 2H), 4.8 (s, 3H), 5.2 (t, 1H), 7.2 (s, 1H), 7.3 (s, 3H), 8.75 (s, 1H)

EXAMPLE 13

4-[2-(2'-chlorophenyl)-1-hydroxyethyl]-5-methyl-imidazole $^1$H-NMR (HCl-salt): 1.65 (s, 3H), 3.05 (d, 2H), 4.6 (s, 3H), 5.0 (t 1H), 7.0 (m, 4H), 8.4 (s, 1H)

EXAMPLE 14

4-[2-(2',6'-dichlorophenyl)-1-hydroxyethyl]-5-methyl-imidazole

M.p. of hydrochloride 193°–195° C. (from water)

$^1$H-NMR: 1.5 (s, 3H), 3.3 (d, 2H), 4.3 (s, 2H), 5.1 (t, 1H), 7.0 (s, 3H), 8.4 (s, 1H)

EXAMPLE 15

4-[2-(3'-methylphenyl)-1-hydroxyethyl]-imidazole

M.p. of hydrochloride 142°–145° C.

$^1$H-NMR (HCl-salt): 2.2 (s, 3H), 3.05 (d, 2H), 4.65 (s, 3H), 5.05 (t, 1H), 6.9–7.2 (m, 5H), 8.55 (s, 1H).

EXAMPLE 16

4-[3-(2',6'-dimethylphenyl)-1-hydroxypropyl]-5-methyl-imidazole

M.p. of hydrochloride 166°–168° C.

$^1$H-NMR (HCl-salt): 2.1 (s, 6H), 2.25 (s, 3H), 4.8 (s, 3H), 6.8 (s, 3H), 8.6 (s, 1H)

EXAMPLE 17

4-[2-(2',6'-dimethylphenyl)-1-hydroxyethyl]-imidazole

Melting point of hydrochloride 179°–181° C.

$^1$H-NMR: 2.2 (s, 6H), 3.2 (d, 2H), 4.7 (s, 3H), 5.05 (t, 1H), 7.1 (s, 3H), 7.2 (s, 1H), 8.6 (s, 1H).

EXAMPLE 18

4-(3-phenyl-1-hydroxypropyl)-5-methyl-imidazole

M.p. of the base 134°–136° C.

EXAMPLE 19

4-[2-(2',3'-dimethylphenyl)-1-hydroxyethyl]-5-methyl-imidazole

M.p. of the base 167°–171° C., M.p. of the hydrochloride 173°–175° C.

EXAMPLE 20

4-(2-phenyl-1-hydroxyethyl)-5-methyl-imidazole

M.p. of the base 111°–120° C. M.p. of the hydrochloride 154°–156° C.

EXAMPLE 21

4-[3-(2',4',6'-trimethylphenyl)-1-hydroxypropyl]-imidazole

M.p. of the hydrochloride 153°–155° C. (from isopropanol).

EXAMPLE 22

4-[2-(4'-methylphenyl)-1-hydroxyethyl]-imidazole

M.p. of the base 152°–154° C. (from isopropanol).

EXAMPLE 23

4-[3-(4'-ethylphenyl)-1-hydroxypropyl]-imidazole

M.p. of the hydrochloride 124°–129° C. (from ethylacetate).

EXAMPLE 24

4-(2-phenyl-1-hydroxyethyl)-imidazole

M.p. of the base 155°–157° C. (from isopropanol).

EXAMPLE 25

4-[4-(2',6'-dichlorophenyl)-1-hydroxybutyl]-imidazole

M.p. of the base 53°–55° C.

EXAMPLE 26

4-[2-(2'-methylphenyl)-1-hydroxyethyl]-imidazole

M.p. of the base 149°–151° C. (from isopropanol). M.p. of the hydrochloride 176°–178° C. (from ethanol).

EXAMPLE 27

4-[2-(2',6'-dimethylphenyl)-1-hydroxyethyl]-5-methyl-imidazole

M.p. of the hydrochloride 177°–179° C.

EXAMPLE 28

4-[3-(2',6'-dimethylphenyl)-1-propenyl]-imidazole 10 g of 4-[3-(2',6'-dimethylphenyl)-1-hydroxypropyl]-imidazole is refluxed in 100 ml of concentrated hydrochloric acid for 10 hours. After cooling, the solution is extracted with chloroform. The combined chloroform extracts are washed with 10 percent hydroxide solution, then with water, dried and evaporated to dryness.

The residue which is crude product is purified further by column chromatography using a Merck's reversed phase column, eluting the column with methanol. The melting point of the product is 162°–168° C. (as hydrochloride from ethyl acetate).

$^1$H-NMR (HCl-salt): 1.9 (s, 6H), 3.1 (d, 2H), 4.65 (s, 2H), 5.5–6.1 (m, 2H), 6.5 (s, 1H), 6.6 (s, 3H), 8.35 (s, 1H)

EXAMPLE 29

4-[3-(2',6'-dimethylphenyl)-propyl]-imidazole 5 g of 4-[3-(2',6'-dimethylphenyl)-1-hydroxypropyl]-imidazole is refluxed for 5 hours in 50 ml of conc. hydrochloric acid. The solution is cooled, 0.2 g of 10 percent palladium on carbon is added and the reaction mixture is stirred vigorously in hydrogen atmosphere at room temperature for as long as hydrogen is consumed. The mixture is then filtered and the filtrate is distilled to dryness. 50 ml of water is added and the solution is extracted with chloroform. The chloroform extract is washed with water, then with about 5 percent sodium hydroxide solution and finally with water and evaporated to dryness. The crude product is dissolved in toluene and HCl-ethyl acetate is added to precipitate the product as hydrochloride. Yield 3.8 g (82 percent); m.p. 185°–187° C. (from water).

$^1$H-NMR (HCl-salt): 1.3 (m, 2H), 1.9 (s, 6H), 2.3 (m, 4H), 4.6 (s, 2H) 6.6 (s, 3H), 6.65 (s, 1H), 8.6 (s, 1H).

MS: 214 (18%), 133 (7%), 119 (13%), 117 (7%), 115 (6%), 105 (5%), 95 (90%), 91 (13%), 82 (100%), 81 (91%).

In the examples 30–34 the procedure of Example 29 is repeated except that in place of 4-[3-(2',6'-dimethylphenyl)-1-hydroxypropyl]-imidazole is used in the Examples 30–33 the corresponding 4-[(substituted-phenyl)-1-hydroxyalkyl]-imidazole and in the Example 34 is used 4-[2-(2',6'-dimethylphenyl)-1-hydroxyethyl]-5-methyl-imidazole.

EXAMPLE 30

4-[3-(2',4'-dimethylphenyl)-propyl]-imidazole $^1$H-NMR: 1.9 (m, 2H), 2.15 (s, 3H), 2.2 (s, 3H), 2.5 (m, 4H), 6.7–7.05 (m, 4H), 7.5 (s, 1H), 11.9 (s, 1H)

EXAMPLE 31

4-[3-(3'-methylphenyl)-propyl]-imidazole $^1$H-NMR: 2.0 (m, 2H), 2.2 (s, 3H), 2.55 (m, 4H), 6.75 (s, 1H), 7.0 (m, 4H), 7.5 (s, 1H), 11.7 (s, 1H)

EXAMPLE 32

4-[3-(2',3'-dimethylphenyl)-propyl]-imidazole $^1$H-NMR: 2.0 (m, 2H), 2.1 (s, 3H), 2.2 (s, 3H), 2.6 (m, 4H), 6.8–7.1 (m, 4H), 7.5 (s, 1H), 13 (s, 1H)

EXAMPLE 33

4-[5-(2',6'-dimethylphenyl)-pentyl]-imidazole $^1$H-NMR: 1.45 (m, 6H), 2.2 (s, 6H), 2.55 (m, 4H), 6.7 (s. 1H), 6.9 (s, 3H) 7.9 (s, 1H), 11.8 (s, 1H)

EXAMPLE 34

4-[2-(2',6'-dimethylphenyl)-ethyl]-5-methyl-imidazole

M.p. of the hydrochloride 244°–247° C.

$^1$H-NMR: 1.99 (s, 3H), 2.23 (s, 6H), 2.88 (t, 4H), 4.99 (s, 2H), 7.04 (s, 3H), 8.62 (s, 1H)

EXAMPLE 35

4-[2-(2',6'-dimethylphenyl)-ethyl]-imidazole (a) 2-(2',6'-dimethylphenyl)ethylglyoxal diethyl acetal 9 g of magnesium turnings are covered with 400 ml of dry tetrahydrofuran and the mixture is warmed to boiling. To that mixture is then added 2-(2',6'-dimethylphenyl)-1-bromoethane at such a rate that a gentle boiling is maintained. When the magnesium turnings have reacted the solution containing the Grignard reagent is cooled to room temperature. The reaction mixture is then added dropwise, over a period of 3 hours, to a cooled (0°–5° C.) solution of diethoxyacetic acid piperidinyl amide (80.8 g) in 200 ml of dry tetrahydrofuran. After the addition is complete, the reaction mixture is stirred for two hours at about 5° C. The mixture is then poured into a cold 2% sulfuric acid solution (1000 ml). The solution is extracted with toluene and the combined toluene extracts are washed with water and evaporated to dryness to give a residue of about 95 g. The residue is distilled under reduced pressure. The fore-fraction distilling below 120° C./0.6 mmHg is discarded and the rest, about 66 g, is crude 2-(2',6'-dimethylphenyl)-ethylglyoxal diethyl acetal, which is used without purification in step (b).

(b) 1,1-diethoxy-2-hydroxy-4-(2',6'-dimethylphenyl)-butane 66 g of crude 2-(2',6'-dimethylphenyl)ethylgyoxal diethyl acetal is dissolved in 250 ml of ethanol and 5.0 g of sodium borohydride is added in small portions at a temperature below 30° C. After the addition is complete, the mixture is stirred overnight at room temperature. About 100 ml of ethanol is distilled off and 300 ml of water is added. The solution is extracted with chloroform. The combined chloroform extracts are washed with water, dried with sodium sulfate, and evaporated to dryness. The yield is about 60 g of light reddish brown oil, which is used directly in step (c).

(c) 4-[2-(2',6'-dimethylphenyl)-ethyl]-imidazole 6.0 g of the oil from the preceding step and 150 ml of formamide are combined and stirred at 150° C. while passing ammonia gas into the solution for 6 hours. The mixture is cooled to room temperature and 400 ml of water is added. Concentrated hydrochloric acid is added with cooling until the pH is 3–4.

The solution is washed with toluene, cooled and the pH is adjusted to 10–12 with 20% sodium hydroxide solution. The mixture is extracted with chloroform and the combined chloroform extracts are extracted with 10% acetic acid solution. The combined acetic acid extracts are made alkaline (pH 10–12) while cooling with 20% sodium hydroxide solution. The product is extracted into chloroform, and the combined chloroform extracts washed with water and dried with sodium sulfate. The solution is evaporated to dryness to give 4-[2-(2',6'-dimethylphenyl)-ethyl]-imidazole base, about 24 g.

The hydrochloride is prepared by dissolving the base in ethyl acetate and adding HCl-isopropanol until pH is about 4. The mixture is cooled and filtered and the filter cake washed with a small amount of ethyl acetate. After recrystallisation from a small amount of isopropanol the melting point is 201°–204° C. The base is liberated from the hydrochloride and has the melting point 117°–118° C.

$^1$H-NMR (HCl-salt): 1.9 (s, 6H), 2.6 (s, 4H), 4.95 (s, 2H), 6.6 (s, 3H), 6.95 (s, 1H), 8.5 (s, 1H).

$^{13}$H-NMR (HCl-salt): 19.86 (q), 24.20 (t), 29.12 (t), 116.19 (d), 127.32 (d). 129.02 (d), 133.48 (d), 133.89 (s), 137.52 (s), 137.70 (s)

In the Examples 36–39 the procedure of Example 35 is repeated except that in place of 2-(2',6'-dimethylphenyl)-1-bromoethane is used the appropriate (substituted-phenyl)-1-bromoalkane.

EXAMPLE 36

4-[2-(2'-methylphenyl)-ethyl]-imidazole

Melting point of the hydrochloride 179°–183° C. (from isopropanol)

$^1$H-NMR: 2.2 (s, 3H), 2.8 (s, 4H), 4.75 (s, 2H), 6.95 (s, 1H), 7.0 (s, 4H) 8.45 (s, 1H)

MS: 186 (75%), 185 (17%), 171 (22%), 157 (6%), 142 (6%), 115 (4%), 105 (47%), 104 (8%), 103 (5%), 95 (10%), 91 (4%), 82 (12%), 81 (100%)

EXAMPLE 37

4-[2-(3'-methylphenyl)-ethyl]-imidazole

M.p. 78°–81° C.

$^1$H-NMR (HCl-salt): 2.0 (s, 3H), 2.65 (s, 4H), 4.65 (s, 2H), 6.8 (m, 5H), 8.45 (s, 1H).

EXAMPLE 38

4-[2-(2',3'-dimethylphenyl)-ethyl]-imidazole

M.p. 146°–148° C. (193°–197° C. as hydrochloride)

$^1$H-NMR (HCl-salt): 2.0 (s, 3H), 2.05 (s, 3H), 2.75 (s, 4H), 4.7 (s, 2H) 6.75 (s, 3H), 6.91 (s, 1H), 8.5 (s, 1H)

EXAMPLE 39

4-[4-(2',6'-dimethylphenyl)-butyl]-imidazole

M.p. of hydrochloride 154°–162° C. (from ethylacetate-isopropanol)

$^1$H-NMR (HCl-salt): 1.2 (m, 4H), 1.9 (s, 6H), 2.2 (m, 4H), 4.65 (s, 2H), 6.55 (s, 4H), 8.4 (s, 1H)

$^{13}$H-NMR (HCl-salt): 20.33 (q), 24.67 (f), 28.89 (t), 29.00 (t), 29.77 (t), 115.37 (d), 126.21 (d), 128.73(d), 133.59 (d), 134.30 (s), 136.52 (s), 139.80 (s).

EXAMPLE 40

4-[2-(2',6'-dimethylphenyl)-ethyl]-imidazole

A mixture of 13.0 g of 1-(2',6'-dimethylphenyl)-4-chloro-3,4-epoxybutane and 30 ml of formamide is refluxed for 30 hours. The excess of formamide is distilled off and 20 ml of water is added. The mixture is then made alkaline with sodium hydroxide and extracted with toluene. The combined toluene extracts are washed with water, then with dilute hydrochloric acid. The combined hydrochloric acid extracts are made alkaline with sodium hydroxide and the mixture is extracted with toluene. The toluene extracts are washed with water and evaporated to dryness.

The residue, which is crude 4-[2-(2',6'-dimethylphenyl)-ethyl]-imidazole is transformed to the hydrochloride in ethylacetate by adding an isopropanol solution containing dry hydrogen chloride. The melting point of the hydrochloride is 198°–202° C.

EXAMPLE 41

4-[2-(2',3'-dimethylphenyl)-ethyl]-imidazole

A mixture of 10.0 g of 4-[(2',3'-dimethylphenyl)-ethyl]-N-acetylimidazole and 50 ml of 6N hydrochloric acid is refluxed with stirring for 6 hours. The mixture is distilled to a smaller volume and 50 ml of water is added. The pH is adjusted with sodium hydroxide to 8–9. The precipitate is filtered and washed with water. The product melts at 146° C.

EXAMPLE 42

4-[3-(2',6'-dimethylphenyl)-propyl]-imidazole 10 g 4-[1-chloro-3-(2',6'-dimethylphenyl)-propyl]-imidazole is dissolved in 80 ml of ethanol. 0.1 g of 10% palladium on carbon is added and the reaction mixture is stirred at room temperature in a hydrogen atmosphere until no more hydrogen is consumed. The mixture is then filtered and the filtrate is evaporated to dryness. The residue is dissolved in 30 ml of concentrated hydrochloric acid and the solution is cooled. The precipitate is filtered and washed with a little amount of cold water. The product is obtained in the form of the hydrochloride and melts at 185°–187° C.

EXAMPLE 43

4-[2-(2',3'-dimethylphenyl)-ethyl]-imidazole 10 g of 4-[2-(2',3'-dimethylphenyl)-ethyl]-N-benzyl-imidazole is dissolved in 200 ml of ethanol. 0.2 g of 10% palladium on carbon is added and the reaction mixture is stirred vigorously at 70° C. in a hydrogen atmosphere until the uptake of hydrogen ceases. The mixture is cooled and filtered. The filtrate is evaporated to dryness.

The residue is dissolved in ethylacetate and isopropanol containing dry hydrogen chloride is added until the solution is slightly acidic. The precipitate is filtered and washed with ethylacetate. The hydrochloride of the product melts at 146°–148° C.

In the examples 44–46 the procedure of Example 1 is repeated, except that in place of 2-(2',6'-dimethylphenyl)-1-bromoethane is used the corresponding (substituted phenyl)-1-bromoalkane and in place of 4-imidazolealdehyde is used 5-methyl-4-imidazolealdehyde.

EXAMPLE 44

4-[2-(2',5'-dimethylphenyl)-1-hydroxyethyl]-5-methyl-imidazole

M.p. of the hydrochloride 169°–170° C.

EXAMPLE 45

4-[2-(3',4'-dimethylphenyl)-1-hydroxyethyl]-5-methyl-imidazole.

M.p. of the hydrochloride 161°–163° C.

EXAMPLE 46

4-[3-(4'-methylphenyl)-1-hydroxypropyl]-5-methyl-imidazole

M.p. of the hydrochloride 144°–145° C.

EXAMPLE 47

4-[2-(2',5'-dimethylphenyl)-ethyl]-5-methyl-imidazole

The procedure of Example 29 is repeated except that in place of 4-[3-(2',6'-dimethylphenyl)-1-hydroxypropyl]-imidazole is used 4-[2-(2',5'-dimethylphenyl)-1-hydroxyethyl]-5-methyl-imidazole.

M.p. of the hydrochloride is 190°–192° C.

We claim:

1. A method of treating hypertension, which comprises administering to a subject suffering therefrom or subject thereto an anti-hypertensive effective amount of a substituted imidazole of the general formula:

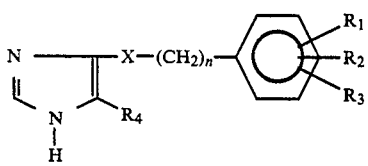

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; X is

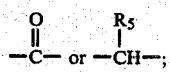

$R_5$ is hydrogen or hydroxy; and n is an integer from 1–4, or of a non-toxic pharmaceutically acceptable acid addition salt thereof.

2. A method of treating thrombosis which comprises administering to a subject suffering therefrom or subject thereto an anti-thrombotic effective amount of a substituted imidazole of the general formula:

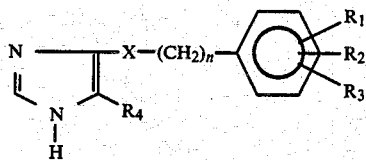

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; X is

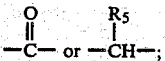

$R_5$ is hydrogen or hydroxy; and n is an integer from 1–4, or of a non-toxic pharmaceutically acceptable acid addition salt thereof.

3. A method of blocking β-receptors in a subject in whom such block may be beneficial which comprises administering to such subject an amount effective to block β-receptors of a substituted imidazole of the general formula:

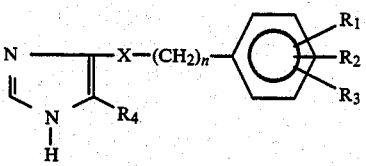

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; X is

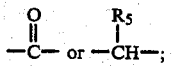

$R_5$ is hydrogen or hydroxy; and n is an integer from 1–4, or of a non-toxic pharmaceutically acceptable acid addition salt thereof.

4. A method according to any one of claims 1, 2 or 3 wherein each of $R_1$, $R_2$ and $R_3$, which can be the same or different, is hydrogen, chloro, methyl, ethyl, methoxy, or hydroxy.

5. A method according to any one of claims 1, 2 or 3 wherein $R_4$ is hydrogen or methyl.

6. A method according to any one of claims 1, 2 or 3 wherein said substituted imidazole is 4-[2-(2',6'-dimethylphenyl)-1-hydroxyethyl]-imidazole or a non-toxic pharmaceutically acceptable acid addition salt thereof.

7. A method according to any one of claims 1, 2 or 3 wherein said substituted imidazole is 4-[2-(2',6'-dichlorophenyl)-1-hydroxyethyl]-5-methyl-imidazole or a non-toxic pharmaceutically acceptable acid addition salt thereof.

8. A method according to any one of claims 1, 2 or 3 wherein said substituted imidazole is 4-[2-(2',6'-dimethylphenyl)-1-hydroxyethyl]-5-methyl-imidazole or a non-toxic pharmaceutically acceptable acid addition salt thereof.

9. A method according to any one of claims 1, 2 or 3 wherein said substituted imidazole is 4-[2-(2'-methylphenyl)-ethyl]-imidazole or a non-toxic pharmaceutically acceptable acid addition salt thereof.

10. A method according to any one of claims 1, 2 or 3 wherein said substituted imidazole is 4-[2-(2',3'-dimethylphenyl)-ethyl]-imidazole or a non-toxic pharmaceutically acceptable addition salt thereof.

11. A method according to any one of claims 1, 2 or 3 wherein said substituted imidazole is 4-[2-(2',6'-dimethylphenyl)-ethyl]-imidazole or a non-toxic pharmaceutically acceptable acid addition salt thereof.

12. A method according to any one of claims 1, 2 or 3 wherein said substituted imidazole is 4-[3-(2',6'-dimethylphenyl)-propyl]-imidazole or a non-toxic pharmaceutically acceptable acid addition salt thereof.

13. A method according to any one of claims 1, 2 or 3 wherein said substituted imidazole is 4-[4-(2',6'-dimethylphenyl)-butyl]-imidazole or a non-toxic pharmaceutically acceptable acid addition salt thereof.

14. A method according to any one of claims 1, 2 or 3 wherein said substituted imidazole is 4-[2-(2',6'-dichlorophenyl)-ethyl]-imidazole or a non-toxic pharmaceutically acceptable acid addition salt thereof.

15. A method according to any one of claims 1, 2 or 3 wherein said substituted imidazole is 4-[2-(2',6'-dimethylphenyl)-1-oxopropyl]-imidazole or a non-toxic pharmaceutically acceptable acid addition salt thereof.

16. A method according to any one of claims 1, 2 or 3 wherein said substituted imidazole is 4-[2-(2',6'-diethylphenyl)-ethyl]-imidazole or a non-toxic pharmaceutically acceptable acid addition salt thereof.

17. A method according to any one of claims 1, 2 or 3 wherein said substituted imidazole is 4-[2-(2'-chlorophenyl)-1-hydroxy-ethyl]-imidazole or a non-toxic pharmaceutically acceptable acid addition salt thereof.

* * * * *